United States Patent
Parikh et al.

(10) Patent No.: US 7,743,769 B2
(45) Date of Patent: Jun. 29, 2010

(54) LARYNGEAL MASK AND METHOD FOR MAKING THE SAME

(75) Inventors: Sanjay Parikh, Finksburg, MD (US); Sarah Lu, Taipei Hsien (TW)

(73) Assignee: Ambu Inc., Glen Burnie, MD (US)

( * ) Notice: Subject to any disclaimer, the term of this patent is extended or adjusted under 35 U.S.C. 154(b) by 709 days.

(21) Appl. No.: 11/730,933

(22) Filed: Apr. 4, 2007

(65) Prior Publication Data

US 2007/0246050 A1    Oct. 25, 2007

Related U.S. Application Data

(60) Provisional application No. 60/788,721, filed on Apr. 4, 2006.

(51) Int. Cl.
*A61M 16/00* (2006.01)
(52) U.S. Cl. .............................. 128/207.15; 128/207.14
(58) Field of Classification Search ................................ 128/207.14–207.16, 206.26, 200.26
See application file for complete search history.

(56) References Cited

U.S. PATENT DOCUMENTS

| 5,297,547 | A   |   | 3/1994 | Brain  | 128/207.15 |
| 6,604,525 | B2  | * | 8/2003 | Pagan  | 128/207.15 |

* cited by examiner

*Primary Examiner*—Steven O Douglas
(74) *Attorney, Agent, or Firm*—Levy & Grandinetti

(57) ABSTRACT

A laryngeal mask including a dome and an airway tube extending from a proximal passage through the dome. The dome has a periphery about its base including at least one receptacle. An inflatable cuff of flexible material has a first longitudinal edge and a second longitudinal edge. The longitudinal edges are joined to form a tube forming the cuff. The cuff substantially encircles the periphery of the dome. The mask has at least one buttress adjacent to the periphery at a distal portion of the dome. The tube is fused adjacent the buttress of the dome, and the fusing is below a posterior surface of the dome wherein, upon deflation of the cuff, the buttress upturns the cuff to facilitate insertion of the laryngeal mask into a patient.

8 Claims, 7 Drawing Sheets

LARYNGEAL MASK AND METHOD FOR MAKING THE SAME

We claim the benefit under Title 35, United States Code, §119, of U.S. Provisional Application Ser. No. 60/788,721, filed Apr. 4, 2006, entitled LARYNGEAL MASK AND METHOD FOR MAKING SAME.

BACKGROUND OF THE INVENTION

1. Field of the Invention

This invention relates to a laryngeal mask and method for making such a mask. Specifically, this invention relates to a laryngeal mask with a sanitary, air-tight seal between the dome and tubular cuff that form the mask.

2. Description of Related Art

Laryngeal masks are well known and are commonly used by medical and emergency medical personnel to intubate an unconscious patient for anesthetic and ventilation purposes. A laryngeal mask is inserted into the throat or pharynx of an unconscious patient, such as an accident victim. The laryngeal mask forms a seal around the laryngeal inlet and prevents the epiglottis from blocking the lumen. The laryngeal mask provides an open airway to permit the unconscious patient to breathe and be provided anesthesia.

Laryngeal masks are made by numerous manufacturers and have similar structures for the basic components. These manufacturers use standard terminology for the common components of these devices.

Typically, the basic components of a laryngeal mask include a dome, an airway tube or shaft, and a cuff or rim. The dome is a teardrop-shaped, semi-rigid member wherein the more angular portion of the teardrop shape provides the distal or leading edge for insertion into a patient's larynx. A rigid, yet flexible, tube is inserted into an orifice in the proximal portion of the dome and projects from this rounded portion of the dome. The flexible tube is of sufficient length to traverse a curve or angle from the larynx of a patient to a point outward from the patient's mouth. An inflatable cuff encircles the periphery of the dome and is made of soft, flexible material. When the dome is positioned in the larynx of the patient, the cuff is inflated and forms a seal with the surrounding tissue in the upper esophageal sphincter, pyriform fossae, and esophageal inlet to secure the laryngeal mask in place and to ensure that the internal lumen of the mask is positioned over the laryngeal inlet. Various sizes of laryngeal airway devices are available to accommodate different sizes of patients which include both children and adults. It is desirable that the laryngeal mask be constructed of medical-grade materials that can withstand repeated autoclaving to allow repeated use of the laryngeal mask device. Lesser medical-grade materials can be used for single-use or "disposable" laryngeal mask devices.

The industry strives to improve these individual components as well as the collateral components used in these devices. Collateral components include inflation tubes for the cuff, devices for inserting the laryngeal mask without damaging nerve or other structures, and similar components.

U.S. Pat. No. 5,297,547 to Brain discloses a laryngeal mask construction. The improvement of this patent focuses on "an inflatable ring configured, upon inflation, to establish a peripheral seal around a patient's laryngeal inlet. Installation (insertion) is made in the fully deflated state, wherein the structural relation between the body of the mask and the inflatable ring is such that the deflated ring surfaces become tightly opposed to each other so as to form a thin flange which peripherally surrounds the body of the mask and is concave on the posterior side of the mask; the concave flange effectively displaces all ring material away from the aperture of the mask, in the manner of the upturned brim of a hat." The invention of this patent approached this problem by placing an excess or bead of filler in the V-shaped area formed between the body (dome) and ring (cuff) of the device. The excess filler enables body stiffness to extend preferentially over posterior material of the ring. This excess bead of filler, however, forms two creases within the narrow V-shaped area wherein contaminants and/or microbes can collect.

The industry lacks a sanitary means and a method for manufacturing a secure air-tight seal between the cuff or tubular structure and dome of laryngeal masks wherein the flexible wall of the cuff is buttressed such that, when deflated, it forms a shape or geometry that facilitates the insertion of the laryngeal mask into the throat of a patient.

The industry also lacks a method for making a secure air-tight seal between the cuff and dome of a laryngeal mask which does not require a protrusion above the seal of continuous filler material to form a buttress for the cuff.

SUMMARY OF THE INVENTION

A laryngeal mask includes a dome and an airway tube extending from a proximal passage through the dome. The dome has a periphery about its base including at least one receptacle. An inflatable cuff of flexible material has a first longitudinal edge and a second longitudinal edge. The longitudinal edges are joined to form a tube forming the cuff. The cuff substantially encircles the periphery of the dome. The mask has at least one buttress adjacent to the periphery at a distal portion of the dome. The tube is fused adjacent the buttress of the dome, and the fusing is below a posterior surface of the dome wherein, upon deflation of the cuff, the buttress upturns the cuff to facilitate insertion of the laryngeal mask into a patient.

Desirable embodiments of the invention form a seal between the tubular structure and the perimeter of the mask by providing at least one groove between at least two ridges in the perimeter or periphery of a mask. The tubular structure has a cross section whereby the flexible material forms a ring when two complementary edges of the flexible material are interlocked together. The size and geometry of the interlocked joint of the flexible material desirably complement the groove about the periphery of the mask. An adhesive holds the complementary edges of the flexible material together and secures these joined complementary edges within the groove of the periphery of the mask. The structure formed by the ridges of the mask holding the complementary edges of the flexible material forms a solid buttress against which the flexible wall of the tubular structure can be collapsed. The buttress permits the collapsed tubular structure to form a complementary shape suitable for inserting the laryngeal mask into the throat of the patient.

More particularly, the present invention is directed to a seal for a laryngeal mask comprising a dome including at least one channel and at least one distal buttress. The present invention includes an inflatable cuff of flexible material with a first and a second longitudinal edge, one of said longitudinal edges includes a semi-rigid bead, the semi-rigid bead is held by a complementary groove on the other longitudinal edge to form a tube for the cuff. The cuff substantially encircles the periphery of the dome. An adhesive holds the joined semi-rigid bead and complementary channel adjacent to and/or below the buttress of the dome and provides a substantially planer posterior surface between the dome and the cuff.

The method of this invention includes providing at least one groove between at least two ridges at the perimeter of a mask and then sealing the complementary edges of a flexible material with adhesive while inserting the joined complementary edges into a receiving groove of a mask.

DETAILED DESCRIPTION OF THE INVENTION

Figure 1:
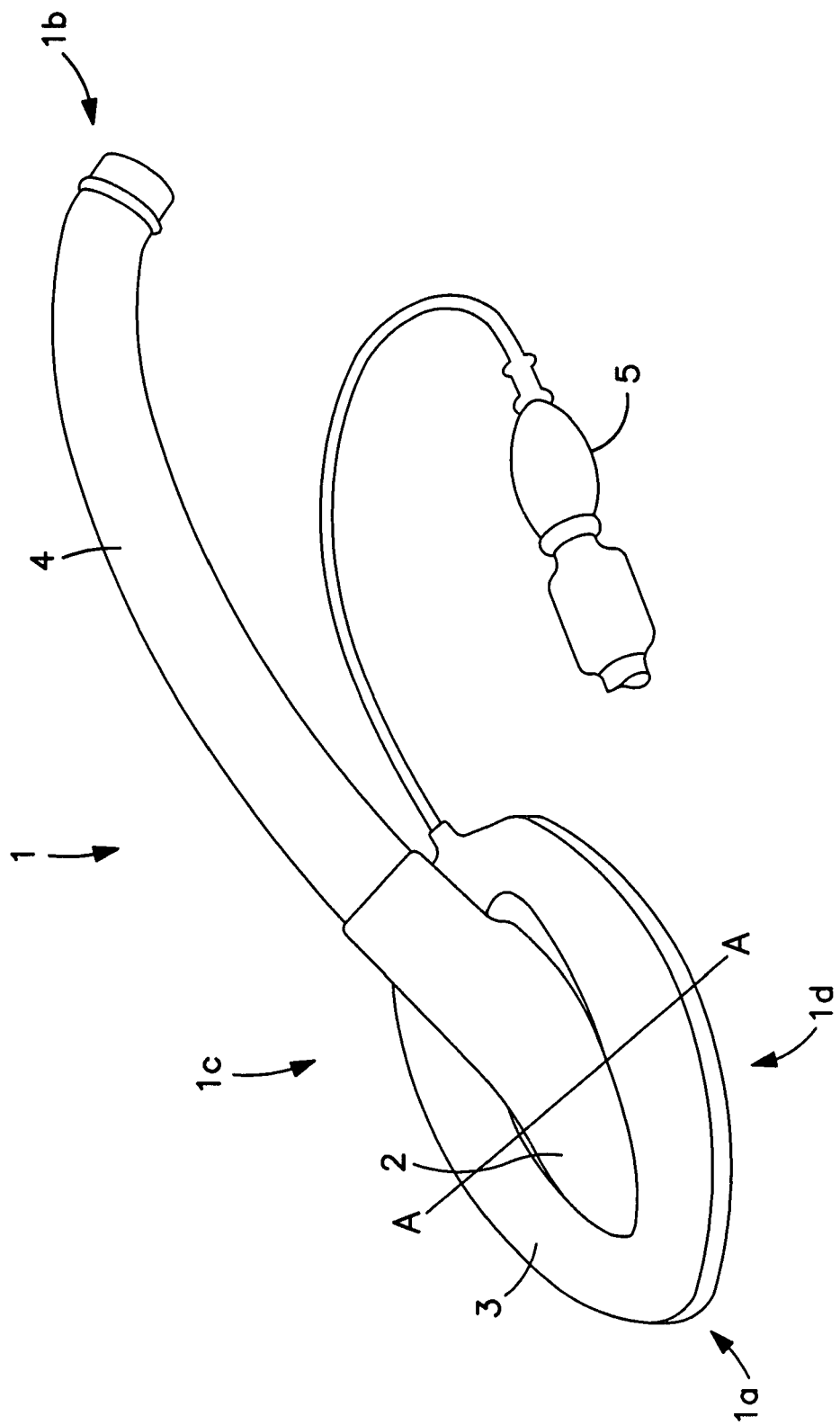
FIG. 1 is a perspective view of the laryngeal mask of the invention.

The invention is a laryngeal mask and method for making such a mask. The laryngeal mask includes a dome, a cuff, and an air tube or passageway. The dome has a periphery at its base. The cuff encircles the base. The invention incorporates at least one buttress adjacent the periphery of at least the distal portion of the dome. Adhesive is used such that it is below a posterior surface of said dome. The adhesive is combined with the cuff and dome so as to provide an airtight seal, which is sanitary and simple to clean. The airtight seal is sanitary because the adhesive does not form crevices with other elements of the laryngeal mask, wherein dirt or microbes can collect. The adhesive positions or holds the cuff adjacent to the buttress such that, upon deflation of the cuff, the buttress upturns the cuff to a shape which facilitates the insertion of the laryngeal mask into the patient.

A desirable embodiment of the invention forms a seal between the tubular structure and the perimeter of the mask by providing at least one receptacle or groove between at least two ridges in the perimeter of a mask. The tubular structure has a cross section whereby the flexible material forms a ring when two complementary edges of the flexible material are interlocked together. The size and geometry of the interlocked joint of the flexible material desirably complement the groove about the perimeter of the mask. An adhesive holds the complementary edges of the flexible material together and secures these joined complementary edges within the groove of the perimeter of the mask. The structure comprised of the ridges of the mask holding the complementary edges of the flexible material forms a solid buttress against which the flexible wall of the tubular structure can be collapsed. The buttress permits the collapsed tubular structure to form a complementary shape suitable for inserting the laryngeal mask into the throat of the patient. The laryngeal mask is positioned in the larynx of the patient. The cuff is inflated and forms a seal with the surrounding tissue in the upper pharynx and esophageal inlet to secure the laryngeal mask in place.

More particularly, the present invention is directed to a seal for a laryngeal mask comprising a dome with a periphery which has a channel and at least one distal buttress. The laryngeal mask also has an inflatable cuff of flexible material with a first and a second longitudinal edge, one of said longitudinal edges includes a semi-rigid bead, said semi-rigid bead is held by a complementary groove on said other longitudinal edge to form a tube for the cuff. The cuff substantially encircles the periphery of the dome. An adhesive holds the semi-rigid bead and complementary channel adjacent to the buttress of the dome, and provides a substantially planer posterior surface between said dome and said cuff.

Preferably, the present invention can be constructed in any geometric shape including a semi-circle, half of a rectangle or square, or a triangle, and the complementary groove on said other longitudinal edge is the complementary inverse of the geometric shape of said semi-rigid bead.

FIG. 1 illustrates a laryngeal mask 1 according to the invention having a distal end 1a, proximal end 1b, posterior portion 1c, and anterior portion 1d. The laryngeal mask includes a dome 2 having a cuff 3. An airway tube 4 is tightly secured to the posterior proximal portion of the dome 2. An inflation means 5 is attached to the proximal end of the cuff 3 and is adapted for connecting with a pump for inflation (not shown).

Figure 2:
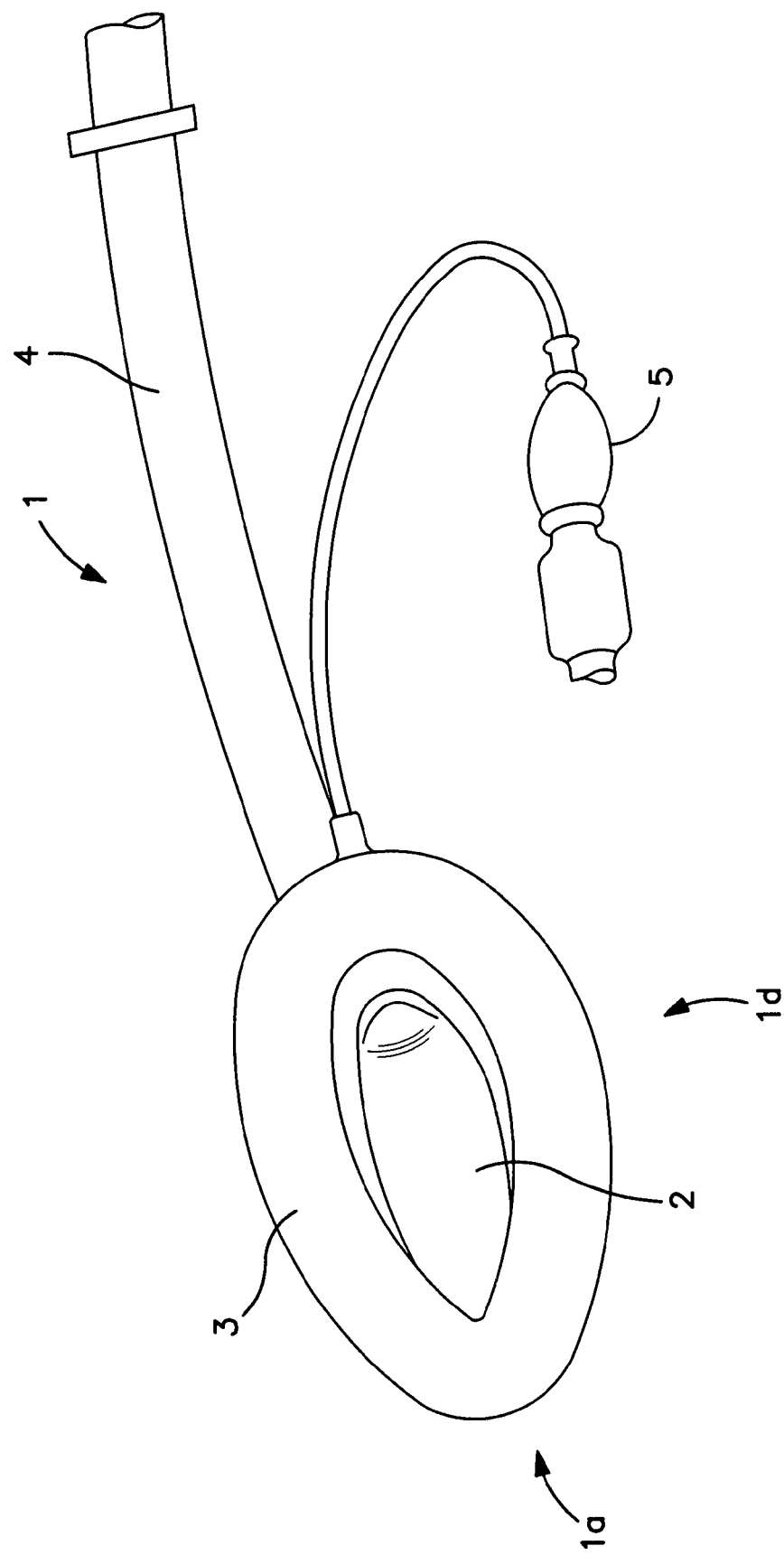
FIG. 2 is the reverse view of FIG. 1.

FIG. 2 illustrates an anterior view of the laryngeal mask 1. This view of the invention demonstrates the passage through the dome 2 into the airway tube 4. The attachment of the airway tube 4 to the dome 2 must be secure such that no separation is possible when the laryngeal mask is being removed from a patient. This figure also illustrates the preferred attachment of the inflation means 5 to the proximal end of the cuff 3. This figure illustrates the cuff 3 in an inflated condition.

Figure 3:
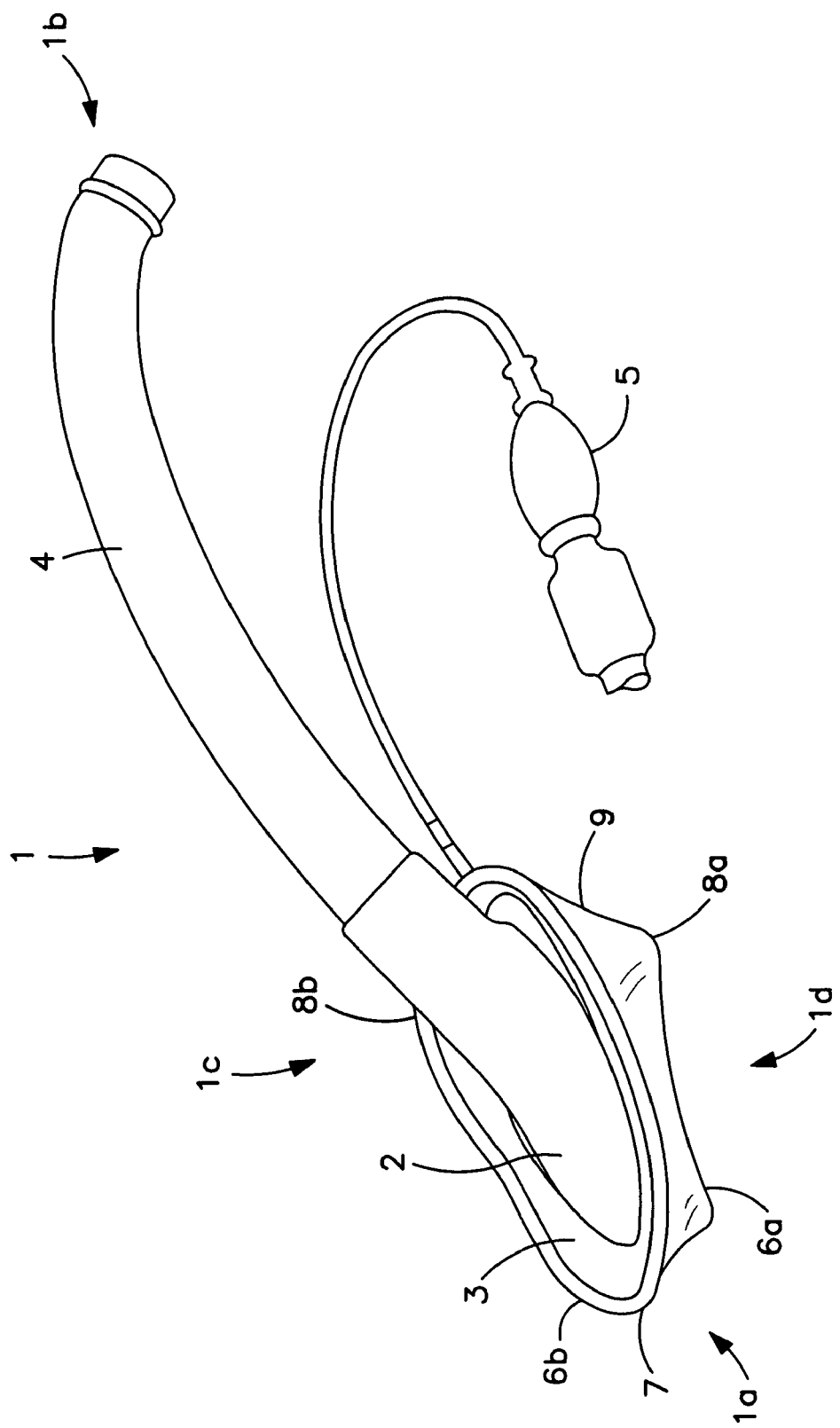
FIG. 3 is a perspective view of the laryngeal mask with the cuff deflated.

FIG. 3 illustrates the laryngeal mask 1 with the cuff 3 in a deflated condition. The cuff 3 is deflated to reduce its overall size and to form a shape which facilitates the insertion of the laryngeal mask 1 into the hypopharynx of a patient. It is desirable for the cuff 3 to deflate uniformly as well as consistently after repeated uses. A desirably deflated cuff 3 collapses in complementary distal portions 6a and 6b. The collapse of the cuff 3 in complementary distal portions 6a and 6b forms an angular shape to facilitate insertion into a patient's upper esophageal opening. It is desirable for the distal tip 7 to be firm enough to separate the epiglottis from the posterior hypopharynx. However, it is also important that the distal tip 7 be sufficiently soft so as not to damage these physiological structures or the lingual nerve.

The deflated cuff 3 also deflates in complementary lateral portions 8a and 8b. The collapse of the cuff 3 on its lateral portions reduces the cross section of the laryngeal mask being inserted into a patient's esophagus. The cross section of the collapsed cuff 3 and dome 2 of the laryngeal mask 1 desirably does not exceed the internal diameter of the patient's esophagus. It is common for laryngeal masks, including those according to the invention, to be manufactured in a variety of sizes because of variations in the internal diameters of patients' esophagi. However, careful selection of the dimensions of the dome 2 and cuff 3 can provide a universal laryngeal mask for most adult patients. For infants, manufacturers typically provide pediatric-sized laryngeal masks.

The deflated cuff 3 also collapses at distal portion 9. Distal portion 9 is desirably the location where the inflation means 5 securely connects to the cuff 3.

Figure 4:
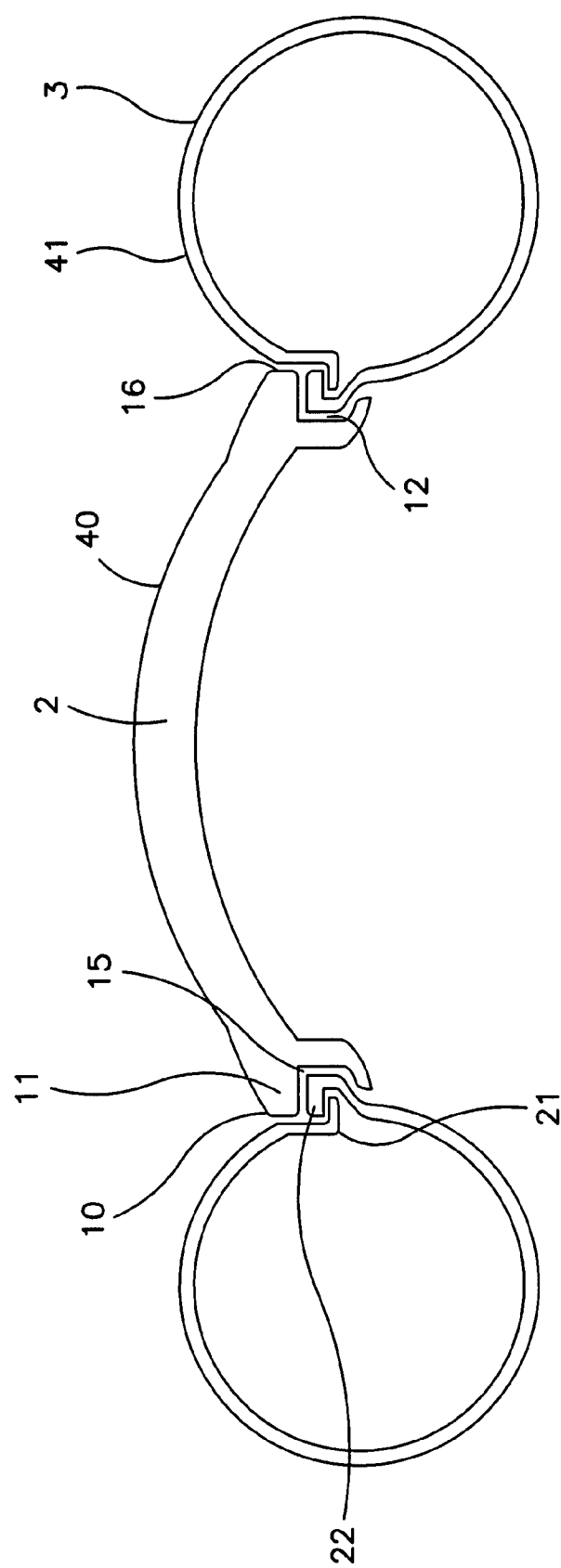
FIG. 4 shows a cross section of the dome and tubular structure of the laryngeal mask of FIG. 1.

FIG. 4 illustrates a lateral cross section along reference line A of FIG. 1 of the dome 2 and inflated cuff 3 of the preferred embodiment of the invention. The dome 2 has a teardrop-shaped geometry when viewed anteriorly, as shown in FIG. 2. The cuff 3 is formed from strips of flexible material. A periphery 10 encircles the base of the dome 2 and forms the teardrop shape. The dome 2 has at least one buttress 11 at the distal portion of the periphery 10. Desirable embodiments include a buttress that encircles the periphery 10 of the dome 2. The buttress 11 can provide part of or include a receptacle 12 for receiving the cuff 3. The dome 2 of the preferred embodiment forms a receptacle 12 from the anterior buttress surface 15 with a J-shaped flange 16. In the preferred embodiment the buttress 11 and J-shaped flange 16 fully encircle the periphery 10 of the dome 2. The invention includes embodiments where one or both of the buttress 11 and J-shaped flange 16 partially encircle the periphery 10.

Figure 5:
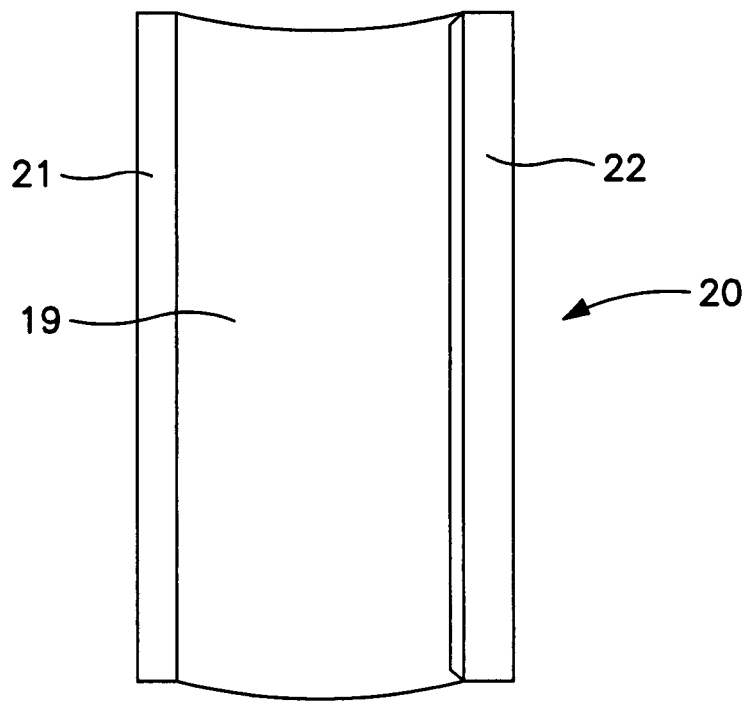
FIG. 5 is a top view of the flexible sheet for the cuff.

FIG. 5 illustrates a top view of a cuff 3 wherein the flexible material 19 of the cuff is in a flat condition 20. The flexible material 19 has a first longitudinal edge 21 and a second longitudinal edge 22. The dimensions and sizes of the respective longitudinal edges are complementary such that the formation of a tubular structure of the flexible material 19 is completed by the joining of the first longitudinal edge 21 into the second longitudinal edge 22. The complementary longitudinal edges desirably have complimentary bead-like structures with ridges and receptacles, but certain embodiments of the invention can form a cuff from a flat sheet of flexible material. The flexible material 19 is desirably a soft polymer such as latex, polyurethane, or similar natural or synthetic resin material.

Figure 6:
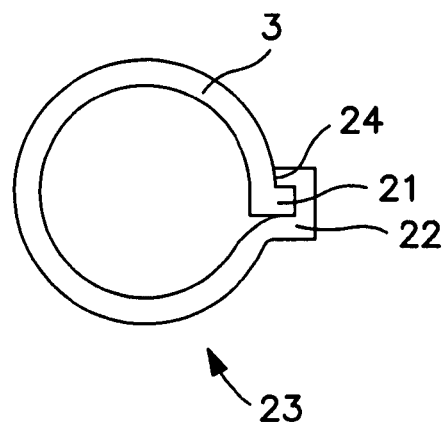
FIG. 6 is a cross section of the joinder of the preferred longitudinal edges of the flexible sheet of the cuff.

FIG. 6 illustrates the preferred embodiment of complementary geometries and sizes of the respective longitudinal edges just prior to being joined. Examples of such complementary geometries include circular, rectangular, square, triangular, and irregular geometries with their respective inverse geometric shape. The first longitudinal edge 21 in this embodiment is a semi-rigid bead pressed against the complementary semi-rigid canal or receptacle of the second longitudinal edge 22 as the flexible material 19 is curled into a tubular condition 23. The face 24 of the second longitudinal edge 22 is adjacent to the flexible material 19 and can act in full or in part as the buttress 11 in embodiments of the invention. The joining of the longitudinal edges is preferably facilitated with adhesive (not shown). Frictional tension, such as that provided with a snap-fit or a "zip-lock" structure, can be used. The formation of the cuff into a tubular shape must be sufficiently secure and air-tight that its inflation during use of the laryngeal mask will not rupture the seal formed by the joining of the longitudinal edges.

Figure 7:
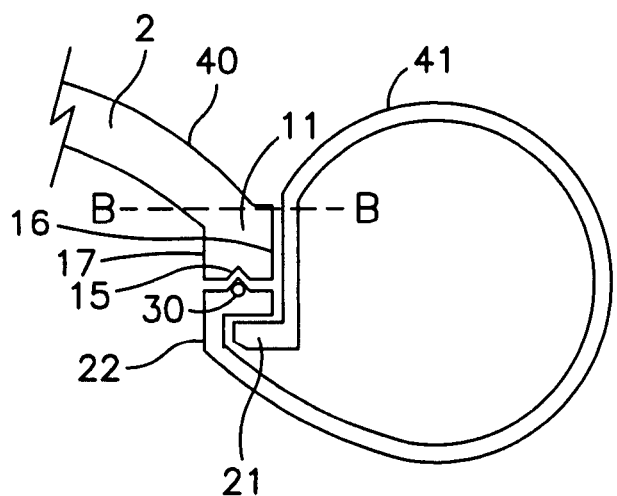
FIG. 7 is a cross section of an alternative embodiment of a dome and cuff.
Figure 8:
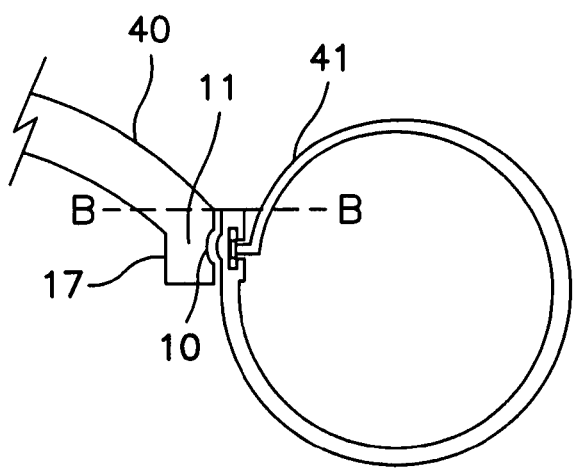
FIG. 8 is a cross section of another alternative embodiment of a dome and cuff.

FIGS. 7 and 8 illustrate cross sections of alternative embodiments of the periphery 10 and buttress 11 of the invention and structures for joining the cuff 3 to the periphery 10 of the dome 2. Various geometries can be used to form the edges to seal the cuff 3 and to seal the cuff 3 to the periphery 10 of the dome 2. The cuffs, which can be circular, oval, or other desirable shapes, are typically joined to the periphery 10 by fusing the polymer material by an adhesive or, with certain polymers, welding. In certain embodiments, the cuff can snap-fit into a periphery.

FIG. 7 illustrates a buttress 11 wherein the joined edges of the cuff 3 are attached to the anterior buttress surface 15. First longitudinal edge 21 complements and inserts into the second longitudinal edge 22. In this embodiment, the second longitudinal edge 22 has an optional ridge 30 which engages complementary groove 31 in the anterior buttress surface 15.

FIG. 8 illustrates a periphery 10 conforms to receive the joined edges of the cuff 3 and one surface of a longitudinal edge provides the buttress 11. The first longitudinal edge 21 of this embodiment snap-fits into the second longitudinal edge 22. The shape of a surface 32 of the second longitudinal edge 22 complements the periphery 10 and can be attached by adhesive or by a snap-fit arrangement. Other alternative embodiments (not shown) can be made according to the invention, such as an attachment of the dome 2 to the interior buttress surface 17.

Figure 9:
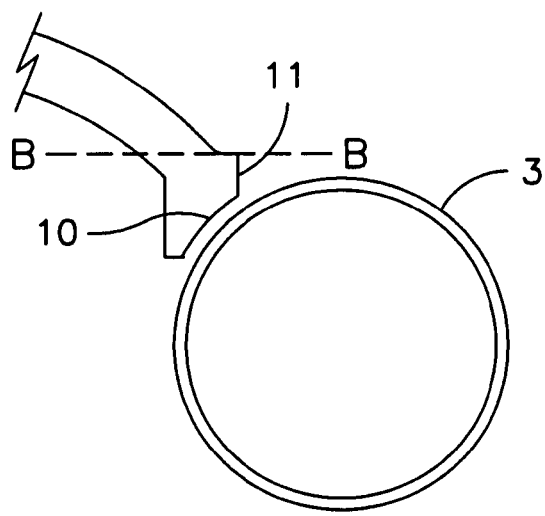
FIG. 9 is a cross section of another alternative embodiment of a dome and cuff.

FIG. 9 illustrates a cuff 3 formed from a flat flexible material. The tubular cuff 3 is adhered to a complimentary periphery 10 on the dome 2. A buttress 11 is provided on the dome 2.

Reference line B in FIGS. 4, 7, 8, and 9 represents a position above which adhesive is not applied. The adhesive is applied below the posterior surface of the dome 2. Above reference line B a V-shaped area is formed by the posterior surface 40 of the dome 2 and the posterior portion 41 of the cuff 3. In the embodiments of FIGS. 4 and 7, it is not necessary to apply adhesive between the periphery buttress surface 16 and the juxtaposed surface of the cuff 3. However, it is desirable to have a thin layer of adhesive between the periphery buttress surface 16 and the juxtaposed surface of the cuff 3 to prevent a crevice, which can collect contaminants or microbes. The absence of adhesive above reference line B prevents the unnecessary exposure of surfaces, which can collect contaminants or microbes.

Figure 10:
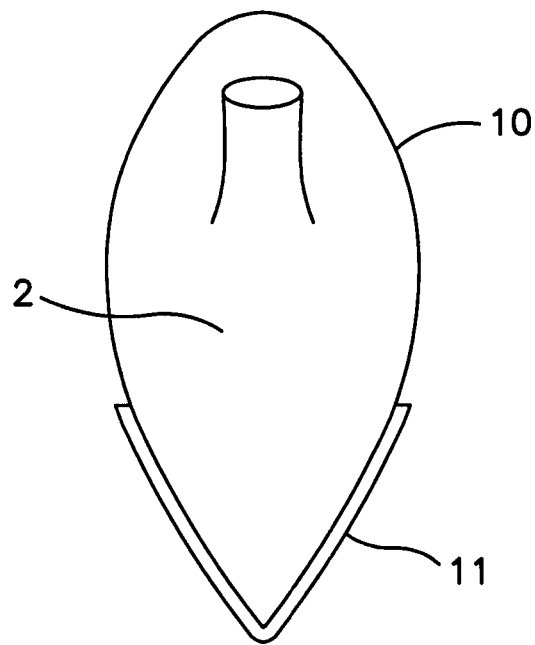
FIG. 10 is a top view of a dome with an alternative buttress.
Figure 11:
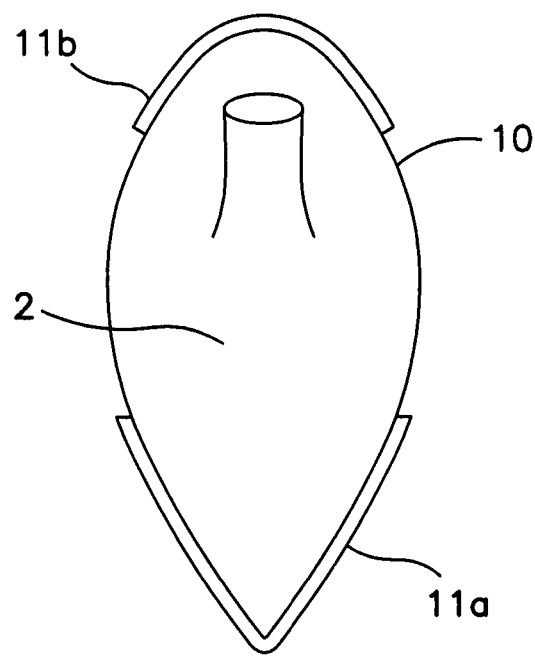
FIG. 11 is a top view of a dome with another alternative buttress.

FIGS. 10 and 11 illustrate alternative embodiments of the invention. These alternative embodiments have at least one buttress 11 which partially encircles the periphery 10 of the dome 2.

FIG. 9 presents an embodiment wherein the buttress 11 partially encircles a distal portion of the periphery 10 of the dome 2. The cuff 3 substantially, but not completely, encircles the periphery 10.

FIG. 10 presents an embodiment wherein two buttresses, 11a and 11b, are present on the periphery 10 of the dome 2. Buttress 11a is present at the distal portion of the periphery 10 and buttress 11b is present at the proximal end of the periphery 10. The cuff 3 (not shown) encircles the entire periphery of this embodiment but is adhered directly to the lateral portion of the periphery 10.

The invention includes a method for manufacturing a laryngeal mask. The method includes providing a dome having a periphery. The periphery of the dome includes at least one buttress. The buttress is present on at least a distal portion of the periphery of the dome.

The method includes forming an inflatable cuff of flexible material. The flexible material has a first longitudinal edge and a second longitudinal edge. The longitudinal edges are complementary such that they join when the flexible material is curved to form a tubelike structure. The longitudinal edges can be joined by friction fit and/or adhesive and provide a secure airtight seal.

The method further includes adhering the semi-rigid structure of the joined complementary longitudinal edges to the buttress of the dome. The method prevents adhesive from the V-shaped area formed by the posterior surface of the dome and the posterior portion of the cuff.

The benefit of this invention is that it provides a simple, reliable structure that is securely sealed and can be repeatedly used as a laryngeal mask. The invention eliminates the need for providing or peripherally including a continuous filler in the V-shaped section formed above the buttress between the outer wall of the mask and a portion of the flexible material of the tubular structure.

We claim:

1. A laryngeal mask comprising:
   a dome, said dome having a periphery about its base, said periphery including at least one receptacle;

an airway tube extending from a proximal passage through said dome;

an inflatable cuff of flexible material, said flexible material has a first longitudinal edge and a second longitudinal edge, said first longitudinal edge and said second longitudinal edge are joined to form a tube for said cuff, said cuff substantially encircles said periphery of said dome;

at least one buttress adjacent said periphery at a distal portion of said dome; and a fusing of said tube forming said cuff, said fusing being adjacent to said buttress of said dome, said fusing is below a posterior surface of said dome wherein, upon deflation of said cuff, said buttress upturns said cuff to facilitate insertion of said laryngeal mask into a patient.

2. The laryngeal mask of claim 1 wherein said buttress is on said periphery of said dome.

3. The laryngeal mask of claim 2 wherein said fusing is adhesive.

4. A laryngeal mask comprising:

a dome, said dome having a periphery, said periphery including at least one channel and at least one distal buttress;

an airway tube extending from a proximal passage through said dome;

an inflatable cuff of flexible material, said flexible material has a first longitudinal edge and a second longitudinal edge, one of said longitudinal edges includes a semi-rigid bead, said semi-rigid bead is held by a complementary receptacle on said other longitudinal edge to form a tube for said cuff, said cuff substantially encircles said periphery of said dome; and an adhesive, said adhesive holds said tube forming said cuff adjacent to said buttress of said dome, said adhesive is below a posterior surface of said dome, wherein, upon deflation of said cuff, said buttress upturns said cuff to facilitate insertion of said laryngeal mask into a patient.

5. The laryngeal mask of claim 4 wherein:

said semi-rigid bead has a rectangular portion; and said rectangular portion of said semi-rigid bead is adhered to a complementary, angular receptacle on said other longitudinal edge.

6. The laryngeal mask of claim 5 wherein:

said adhesive holds said joined semi-rigid bead and complementary receptacle adjacent to said buttress of said dome.

7. A laryngeal mask comprising:

a dome, said dome having a periphery;

an airway tube extending from a proximal passage through said dome;

an inflatable cuff of flexible material, said flexible material has a first longitudinal edge and a second longitudinal edge, said first longitudinal edge includes at least one semi-rigid bead, said semi-rigid bead is held by a complementary semi-rigid channel on said second longitudinal edge to form, when joined, a tube for said cuff and at least a partial buttress, said cuff substantially encircles said periphery of said dome; and an adhesive, said adhesive holds said joined semi-rigid bead and complementary channel adjacent said buttress of said dome, said adhesive provides a substantially planer posterior surface between said dome and said cuff wherein said adhesive is below a posterior surface of said dome, and upon deflation of said cuff, said buttress upturns said cuff to facilitate insertion of said laryngeal mask into a patient.

8. The laryngeal mask of claim 7 wherein:

said semi-rigid bead is constructed in any geometric shape including a semi-circle, half of a rectangle or square, a triangle, and complementary groove on said other longitudinal edge is the complementary inverse of the geometric shape of said semi-rigid bead.

* * * * *